United States Patent [19]

Bateson et al.

[11] Patent Number: 5,246,926
[45] Date of Patent: * Sep. 21, 1993

[54] CEPHALOSPORIN DERIVATIVES

[75] Inventors: John H. Bateson; George Burton; Stephen C. M. Fell, all of Betchworth, England

[73] Assignee: Beecham Group p.l.c., England

[*] Notice: The portion of the term of this patent subsequent to Nov. 12, 2008 has been disclaimed.

[21] Appl. No.: 500,397

[22] Filed: Mar. 28, 1990

[30] Foreign Application Priority Data

Mar. 30, 1989 [GB] United Kingdom ............... 8907171
Sep. 14, 1989 [GB] United Kingdom ............... 8920791

[51] Int. Cl.⁵ ............... C07D 501/56; A61K 31/545
[52] U.S. Cl. ............... 514/202; 514/201; 540/221; 540/222; 540/301; 540/205
[58] Field of Search ............... 540/222, 221; 514/201, 514/202

[56] References Cited

U.S. PATENT DOCUMENTS 4,868,173  9/1989  Jung ............... 540/222
5,064,649  11/1991  Burton et al. ............... 540/222

Primary Examiner—Nicholas S. Rizzo
Attorney, Agent, or Firm—Rosenman & Colin

[57] ABSTRACT

β-Lactam compounds of the formula (Ia) including pharmaceutically acceptable salts and in vivo hydrolysable esters, processes for their preparation and their use as antibiotics:

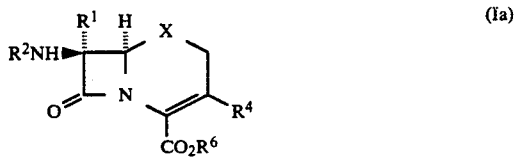

wherein
$R^1$ is hydrogen, methoxy or formamido;
$R^2$ is an acyl group, in particular that of an antibacterially active cephalosporin;
$CO_2R^6$ is a carboxy group or a carboxylate anion;
$R^3$ is a Y-lactone ring optionally containing an endocyclic double bond, which ring is optionally substituted at any carbon atom by alkyl, dialkylamino, alkoxy, hydroxy, halogen or aryl, which in the case of more than one substituent may be the same or different, or is optionally di-substituted at two adjacent carbon atoms, which are available for substitution, to form an aromatic fused bicyclic system; and
X is S, SO, $SO_2$, O or $CH_2$.

15 Claims, No Drawings

CEPHALOSPORIN DERIVATIVES

This invention relates to novel β-lactam containing compounds, their preparation and their use, and in particular to a novel class of cephalosporins. These compounds have antibacterial properties, and therefore are of use in the treatment of bacterial infections in humans and animals caused by a wide range of organisms.

The compound 3-[(acetyloxy)methyl]-7-[2-(2-amino-4-thiazolyl)-2-methoxyiminoacetamido]cephalosporanic acid (cefotaxime) is an injectable, β-lactamase stable, cephalosporin antibiotic. It is representative of a class of cephalosporin compounds known as third generation cephalosporins. Cefotaxime is substituted at the 3-position of the cephalosporin nucleus by a straight-chain, acetyloxymethyl group.

We have now found a particular class of cephalosporins bearing a lactone substituent at the 3-position of the cephalosporin nucleus that possesses high antibacterial activity and also shows good parenteral and oral absorption.

The present invention provides a compound of formula (I) or a salt thereof:

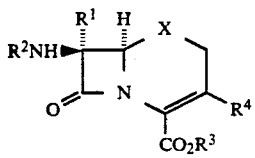

wherein
$R^1$ is hydrogen, methoxy or formamido;
$R^2$ is an acyl group, in particular that of an antibacterially active cephalosporin;
$CO_2R^3$ is a carboxy group or a carboxylate anion, or $R^3$ is a readily removable carboxy protecting group (such as a pharmaceutically acceptable in-vivo hydrolysable ester group);
$R^4$ is a γ-lactone ring optionally containing an endocyclic double bond, which ring is optionally substituted at any carbon atom by alkyl, dialkylamino, alkoxy, hydroxy, halogen or aryl, which in the case of more than one substituent may be the same or different, or is optionally di-substituted at two adjacent carbon atoms, which are available for substitution, to form an aromatic fused bicyclic system; and
X is $S, SO, SO_2, O$ or $CH_2$.

The bonding carbon atom of $R^4$ which links the lactone ring to the cephalosporin nucleus may be asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

As used herein, the term γ-lactone refers to a 5-membered lactone ring bonded via the 3-, 4- or 5-position carbon atom, optionally substituted at the ring carbon atoms as hereinbefore defined, and includes dihydro- and tetrahydro-2-oxofuran rings.

Since the β-lactam antibiotic compounds of the present invention are intended for use as therapeutic agents in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

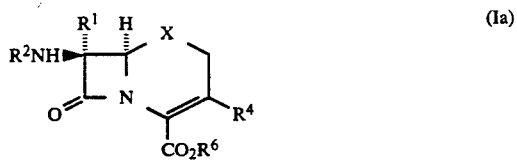

wherein $R^1$, $R^2$, $R^4$ and X are as defined with respect to formula (I) and the group $CO_2R^6$ is $CO_2R^3$ where $CO_2R^3$ is a carboxy group or a carboxylate anion.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $C_{1-6}$ alkyl, phenyl, $C_{1-6}$ alkoxy, hydroxy($C_{1-6}$)alkyl, mercapto($C_{1-6}$)alkyl, halo($C_{1-6}$) alkyl, hydroxy, amino, nitro, carboxy, $C_{1-6}$ alkylcarbonyloxy, alkoxycarbonyl, formyl, or $C_{1-6}$ alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo($C_{1-6}$)alkyl, hydroxy, carboxy, carboxy salts, carboxy esters such as $(C_{1-6})$alkoxycarbonyl, $(C_{1-6})$alkoxycarbonyl($C_{1-6}$)alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein with respect to variable $R^4$, the term 'aromatic fused bicyclic system' falls within the definition of 'fused heterocyclic ring system' as described above, wherein at least one ring is a 5-membered lactone ring. Preferably the second ring is a 5- or 6-membered carbocyclic ring.

When used herein the terms 'alkyl' and 'alkoxy' (or 'lower alkyl' and 'lower alkoxy') include straight and branched chain alkyl groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

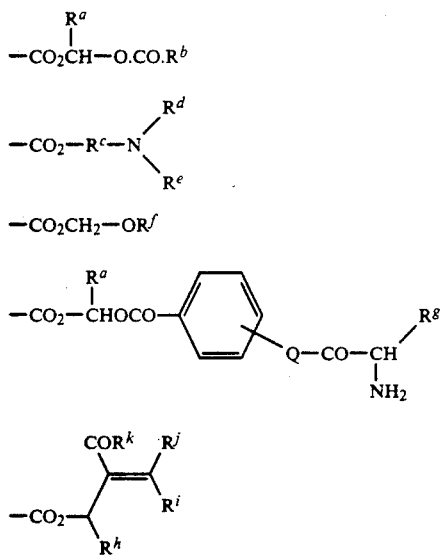

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; Q is oxygen or NH; $R^h$ is hydrogen or $C_{1-6}$ alkyl; $R^i$ is hydrogen, $C_{1-6}$ alkyl optionally substituted by halogen, $C_{2-6}$ alkenyl, $C_{1-6}$ alkoxycarbonyl, aryl or heteroaryl; or $R^h$ and $R^i$ together form $C_{1-6}$ alkylene; $R^j$ represents hydrogen, $C_{1-6}$ alkyl or $C_{1-6}$ alkoxycarbonyl; and $R^k$ represents $C_{1-8}$ alkyl, $C_{1-8}$ alkoxy, $C_{1-6}$ alkoxy($C_{1-6}$)alkoxy or aryl. Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl)but-2-enyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

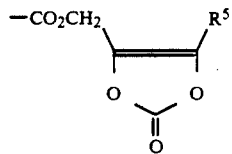

wherein $R^5$ is hydrogen, $C_{1-6}$ alkyl or phenyl.

Suitable pharmaceutically acceptable salts of the carboxy group of the compound of formula (I) include metal salts, eg aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (I) or (Ia), the group X may be sulphur or an oxidised sulphur atom, i.e. a sulphoxide (SO) or sulphone ($SO_2$) group. When X is a sulphoxide group it will be understood that α- and β-isomers may exist; both such isomers are encompassed within the scope of the present invention.

Preferably X is sulphur.

Advantageously, $R^1$ is hydrogen.

Suitable acyl groups $R^2$ include those of formulae (a)-(f):

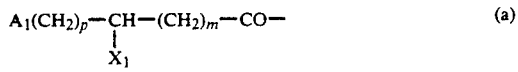

$$\begin{array}{c} \phantom{X_2}\diagup CH_2 \diagdown \phantom{C}\diagup CO- \\ X_2 \phantom{\diagup CH_2 \diagdown} C \\ \phantom{X_2}\diagdown CH_2 \diagup \phantom{C}\diagdown X_1 \end{array} \quad (c)$$

$$A_2-X_3-(CH_2)_p-CO- \quad (d)$$

$$\begin{array}{c} A_3-C-CO- \\ \parallel \\ N \\ \vert \\ OA_4 \end{array} \quad (e)$$

$$\begin{array}{c} A_3-C-CO- \\ \parallel \\ \vert \\ A_4 \end{array} \quad (f)$$

wherein p is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic (including heteroaromatic) group, such as phenyl, substituted phenyl, thienyl, pyridyl, or an optionally substituted thiazolyl group, a $C_{1-6}$ alkylthio group or $C_{1-6}$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a $-CH_2OCH_2-$, $-CH_2SCH_2-$ or alkylene group; $X_3$ is an oxygen or sulphur atom; $A_3$ is an aryl or heteroaryl group such as phenyl, substituted phenyl or aminothiazolyl in which the amino group is optionally protected; and $A_4$ is hydrogen, $C_{1-6}$ alkyl, $C_{3-8}$ cycloalkyl, $C_{1-6}$ alkoxycarbonyl($C_{1-6}$) alkyl, $C_{2-6}$ alkenyl, carboxy($C_{1-6}$)alkyl, $C_{2-6}$ alkynyl, aryl or aryl($C_{1-6}$)alkyl.

The term 'heteroaryl' as used herein means a heteroaromatic heterocyclic ring or ring system, suitably having 5 or 6 ring atoms in each ring.

Suitably when $R^2$ is a group (a), $A_1$ is $C_{1-6}$ alkyl, $C_{3-6}$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is O.

Alternatively when $R^2$ is a group of formula (e), suitable values for the group $A_3$ include those commonly found in antibacterially active cephalosporins containing a hydroxyimino or substituted hydroxyimino group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)-thiazol-4-yl, 2-tritylaminothiazol-4-yl, 5-amino-1,2,4-thiadiazol-3-yl and 4-aminopyrimid-2-yl.

In compounds of formula (Ia), a particularly preferred group for $A_3$ is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the svn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Preferred examples of $R^4$ include 2-oxotetrahydrofuran-5-yl, 2-oxotetrahydrofuran-4-yl and 2-oxotetrahydrofuran-3-yl.

Certain compounds of the invention include an amino group which may be protected. Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following and pharmaceutically acceptable salts and in-vivo hydrolysable esters thereof:

(6R,7R)-7-[2-(2-aminothiazol-4-yl)-2-(Z)-methoxyiminoacetamido]-3-[(5RS)-2-oxotetrahydrofuran-5-yl]ceph-3-em-4-carboxylic acid, (6R,7R)-7-[2-(2-aminothiazol-4-yl)-2-(Z)-hydroxyiminoacetamido]-3-[(5RS)-2-oxotetrahydrofuran-5-yl]ceph-3-em-4-carboxylic acid, (6R,7R)-7-[2-(2-aminothiazol-4-yl)-2-(Z)-methoxyiminoacetamido]-3-[(4RS)-2-oxotetrahydrofuran-4-yl]ceph-3-em-4-carboxylic acid, (6R,7R)-7-[2-(2-aminothiazol-4-yl)-2-(Z)-carboxymethoxy iminoacetamido]-3-[(5RS)-2-oxotetrahydrofuran-5-yl]-ceph-3-em-4-carboxylic acid, and (6R,7R)-7-[2-(2-aminothiazol-4-yl)-2-(Z)-methoxyiminoacetamido]-3-[(3RS)-2-oxotetrahydrofuran-3-yl]ceph-3-em-4-carboxylic acid.

The present invention further provides a process for the preparation of a compound of formula (I), which process comprises treating a compound of formula (II) or a salt thereof:

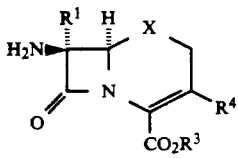
(II)

wherein $R^1$, $CO_2R^3$, $R^4$ and X are as hereinbefore defined, wherein any reactive groups may be protected, and wherein the amino group is optionally substituted with a group which permits acylation to take place; with an N-acylating derivative of an acid of formula (III):

$$R^2OH \quad (III)$$

wherein $R^2$ is as defined with respect to formula (I) and wherein any reactive groups may be protected; and thereafter, if necessary or desired, carrying out one or more of the following steps:
  i) removing any protecting groups;
  ii) converting the group $CO_2R^3$ into a different group $CO_2R^3$;
  iii) converting the group $R^2$ into a different group $R^2$;
  iv) converting the group X into a different group X;
  v) reducing an endocyclic double bond within $R^4$;
  vi) converting the product into a salt.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —$P.R^8R^9$ wherein $R^8$ is an alkyl, haloalkyl, aryl, aralkyl, alkoxy, haloalkyl, aryl, aralkyl, alkoxy, haloalkoxy, aryloxy, aralkyloxy or dialkylamino group, $R^9$ is the same as $R^8$ or is halogen or $R^8$ and $R^9$ together form a ring; suitable such phosphorus groups being —$P(OC_2H_5)_2$, —$P(C_2H_5)_2$,

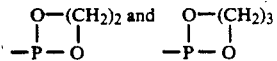

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis(trimethylsilyl)acetamide, N,O-bis(trimethylsilyl)trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°–60° C., preferably 40°–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide-such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) or a salt or a reactive derivative thereof with a halogenating (eg chlorinating or brominating) agent such as phosphorus pentachloride, thionyl chloride, oxalyl chloride or phosgene.

Alternatively, the N-acylating derivative of the acid (III) may be a symmetrical or mixed anhydride. Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, mohomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexyl-carbodiimide, or N-ethyl-N'-[3-(dimethylamino)propyl]-carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at $-40°$ to $+30°$ C., if desired in the presence of an acid binding agent such as pyridine. A catalyst such as 4-dimethylaminopyridine may optionally also be added. A preferred solvent for the above acylation reaction is dichloromethane.

The optional reduction step, the optional conversion of $R^2$ to a different $R^2$, $CO_2R^3$ to a different $CO_2R^3$ and X to a different X, and the optional formation of a salt, may be carried out using methods well known in the art of cephalosporin and penicillin chemistry.

For example, when the group x is S, SO, or $SO_2$, the group X may be converted into a different group X by methods of oxidation or reduction well known in the art of cephalosporin and penicillin synthesis, as described, for example, in European Patent Application Publication No. 0 114 752. For example, sulphoxides (in which X is SO) may be prepared from the corresponding sulphide (in which X is S) by oxidation with a suitable oxidising agent, for example an organic peracid such as m-chloroperbenzoic acid.

A reduction step is generally effected by process of catalytic hydrogenation in the presence of a suitable catalyst or combination thereof.

In the process described hereinabove, and in the process described hereinbelow, it may be necessary to remove protecting groups. Deprotection may be carried out by any convenient method known in the art such that unwanted side reactions are minimised. Separation of unwanted by-products may be carried out using standard methods.

Compounds of formula (II) are novel compounds and as such form part of the invention. Compounds of formula (II) may be prepared by removal of $R^2$ from compounds of formula (I) prepared by the process described hereinbelow.

In a further process of the invention, compounds of formula (I) may be prepared by cyclising a compound of formula (IV):

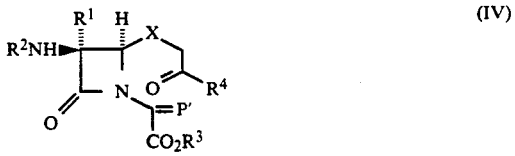

wherein X, $R^1$, $R^2$, $CO_2R^3$ and $R^4$ are as hereinbefore defined and P' is a phosphorus residue; and thereafter if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) reducing an endocyclic double bond within $R^4$;
vi) converting the product into a salt.

The cyclisation reaction is an intramolecular Wittig-type reaction and is typically carried out by heating the compound of formula (IV) in an organic solvent system optionally in the presence of a suitable acid such as benzoic acid.

The phosphorus residue, P' is typically a trialkylphosphoranylidene residue, for example a $C_{1-6}$ trialkylphosphoranylidene residue such as tri-n-butylphosphoranylidene, or a triarylphosphoranylidene residue such as triphenylphosphoranylidene.

A compound of formula (IV) may be prepared from a compound of formula (V):

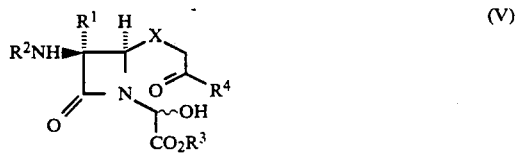

wherein X, $R^1$, $R^2$, $CO_2R^3$ and $R^4$ are as hereinbefore defined, by reaction with a halogenating agent, suitably a chlorinating agent such as thionyl chloride, which reaction displaces the formula (V) hydroxyl group by halogen, suitably chloride, and is typically carried out at reduced temperature in an inert solvent, for example in tetrahydrofuran, in the presence of a base, typically a pyridine derivative such as 2,6-lutidine. Formation of the phosphorane may be effected by treatment of the halo-intermediate with an appropriate phosphine derivative, for example tri-n-butylphosphine or triphenylphosphine, suitably at ambient temperature in an inert solvent such as dioxan.

A compound of formula (V) may be prepared by reaction of the corresponding azetidin-2-one compound of formula (VI):

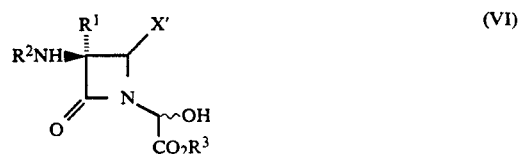

wherein $R^1$, $R^2$ and $CO_2R^3$ are as hereinbefore defined and X' is an X-group precursor (or a leaving group), with a compound of formula (VII):

$$Y-CH_2-C(O)R_4 \qquad (VII)$$

wherein $R^4$ is as hereinbefore defined and Y is a leaving group (or an X-group precursor).

In a typical preparation of a compound of formula (V) in which X is sulphur, a Y leaving group in a compound of formula (VII), suitably a halogen group such as chloro, is displaced by an X mercapto group in a compound of formula (VI). The reaction may be carried out at ambient temperature in an inert solvent, for example acetone, in the presence for a base, for example potassium carbonate.

Azetidin-2-one compounds of formula (VI) may be prepared according to known methods in heterocyclic synthetic chemistry and particularly by known methods in the art of $\beta$-lactam chemistry.

For example, a compound of formula (VI) in which X' is a mercapto group may be prepared by ring opening of a 4-thia-2,6-diazabicyclo[3.2.0]hept-2-ene-7-one derivative according to the method of Masayuki Narisada et al., Tetrahedron Lett., 1755, (1978).

Compounds of formula (VII) are known compounds or may be prepared by standard methodology. For example, the compounds of formula (VII) in which Y is chloro or bromo and $R^4$ is 2-oxotetrahydrofuran-5-yl, 2-oxotetrahydrofuran-4-yl or 2-oxotetrahydrofuran-3-yl may be prepared from the corresponding carboxylic acid (Y=COOH) via formation of the acid chloride followed by treatment with diazomethane and reaction of the resulting diazo compound with hydrogen chloride or hydrogen bromide.

It should be noted that in processes of this invention $\Delta^2$-cephems may function as intermediates, in the synthetic sequences. Subsequent isomerisation steps by methods well known in cephalosporin chemistry will provide the $\Delta^3$-cephems of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (VIII) or a pharmaceutically acceptable salt or ester thereof:

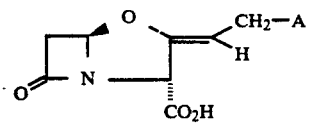

wherein
A is hydroxyl, substituted hydroxyl, thiol, substituted thiol, amino, mono- or di-hydrocarbylsubstituted amino, or mono- or di-acylamino.

A further advantageous composition comprises a compound of formula (Ia) or a pharmaceutically acceptable salt or in vivo hydrolysable ester thereof together with a compound of formula (IX) or a pharmaceutically acceptable salt or in vivo hydrolysable ester thereof:

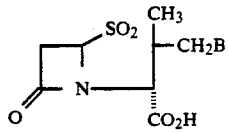

wherein
B represents hydrogen or chloro.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The present invention provides a compound of formula (Ia) or a pharmaceutically acceptable salt or in vivo hydrolysable ester thereof, for use as a therapeutic agent.

The present invention further provides a compound of formula (Ia) or a pharmaceutically acceptable salt or in vivo hydrolysable ester thereof, for use in the treatment of bacterial infections.

The present invention also includes a method of treating bacterial infections in humans and animals which comprises the administration of a therapeutically effective amount of an antibiotic compound of this invention of the formula (Ia) or a pharmaceutically acceptable in vivo hydrolysable ester thereof.

In addition, the present invention includes the use of a compound of formula (Ia) or a pharmaceutically acceptable salt or in vivo hydrolysable ester thereof, for the manufacture of a medicament for the treatment of bacterial infections.

The antibiotic compounds of the present invention are active against a wide range of organisms including both Gram-negative organisms and Gram-positive organisms.

The following Examples illustrate the preparation of the compounds of the present invention and the following biological data illustrate the activity of compounds of the invention in the form of M.I.C. results against a sample E.coli organism (NCTC 10418) and a sample S.aureus organism (S.aureus Oxford).

EXAMPLE 1

Method A (a) t-Butyl (2RS)-2-hydroxy-2-[(1R,5R)-3-phenoxy-methyl-4-thia-2,6-diazabicyclo[3.2.0]hept-2-en-7-one-6-yl]acetate t-Butyl glyoxylate hydrate (4.44g,33mmol) in 1,2-dichloroethane (70 ml) was heated under a Dean and Stark trap containing 4A molecular sieve for 1.5 h, then allowed to cool. (1R,5R)-3-Phenoxymethyl-4-thia-2,6-diazabicyclo[3.2.0]hept-2-en-7-one (6.90 g, 29.5 mmol) (R.D.G. Cooper and F.L. José, *J.Amer.Chem.Soc.*, 1972, 94, 1021), followed by triethylamine (0.42 ml, 2.95 mmol), was added to the t-butyl glyoxylate solution which was then stirred at R.T. for 2h. It was concentrated and flash chromatographed on silica gel, eluting with 40, 50 and 60% ethyl acetate in hexane to give the title compound as a gum (8.04 g, 75%), $v_{max}$ (CH$_2$Cl$_2$) 1780, 1740, 1670 cm$^{-1}$; $\delta_H$ (CDCl$_3$) 1.47 and 1.51 (9H,2s), 4.85–5.1 (2H,m), 5.16 and 5.38 (1H,2s) 5.63 and 5.70 (1H,2d,J4Hz), 6.0–6.1 (1H,m), 6.9–7.4 (5H,m);[mass spectrum: +ve ion (3-nitrobenzylalcohol, sodium acetate) MNa+, 387].

(b) (S)-5-Chloroacetyltetrahydrofuran-2-one

Oxalyl chloride (5.2 ml, 60 mmol) and DMF (2 drops) were added to (S)-2-oxotetrahydrofuran-5-carboxylic acid (6.73 g,5.2 mmol) (A.T. Austin and J. Howard, *J.Chem.Soc.*, 1961, 3593) in dichloromethane (50 ml) and the mixture stirred for 0.5 h. The solvent was removed in vacuo, toluene added to the residue and re-evaporated to provide the acid chloride, $v_{max}$ (CH$_2$Cl$_2$) 1800 cm$^{-1}$.

The acid chloride in ether (100 ml) was added dropwise to an ice bath-cooled solution of diazomethane (80 mmol) in ether (ca.200 ml). The solution was stirred for 0.5 h, then a stream of hydrogen chloride gas passed into it for 0.25 h. It was stirred for a further 0.25 h, then concentrated and flash chromatographed, eluting with 30,35,40% ethyl acetate in hexane to give the title compound as an oil (5.14 g, 61%), $v_{max}$ (film) 1790, 1740 and 1155 cm$^{-1}$; $\delta_H$ (CDCl$_3$) 2.1–2.7 (4H,m), 4.35 (2H,s), 4.9–5.2 (1H,m); [mass spectrum: +ve ion (ammonia) MNH$_4$+, 180].

(c) t-Butyl (2RS)-2-hydroxy-2-4-[(5S)-2-oxotetrahydrofuran-5-ylcarbonylmethylthiol]-3-phenoxyacetamidoazetidin-2-one-1-yl]acetate Toluene-4-sulphonic acid (0.5 g) in water (1.25 ml) was added to t-butyl (2RS)-2-hydroxy-2-(7-oxo-3-phenoxymethyl-4-thia-2,6-diazabicyclo[3.2.0]hept-2-ene-6-yl)acetate (0.55 g) in dichloromethane (2.5 ml) and acetone (2.5 ml) under argon. The mixture was stirred for 2 h, diluted with dichloromethane (30 ml), washed twice with water, dried and evaporated to give crude t-butyl (2RS)-2-hydroxy-2-(4-mercapto-3-phenoxyacetamidoazetidin-2-one-1-yl)acetate as a foam (0.61 g). To this, in acetone (5 ml), was added (S)-5-chloroacetyltetrahydrofuran-2-one (0.326 g, 2 mmol), followed by potassium carbonate (0.104 g,0.75 mmol).

The reaction was stirred for 1 h., diluted with ethyl acetate, washed twice with water and with brine, dried, concentrated and flash chromatographed eluting with 50,60,75,90 and 100% ethyl acetate in hexane to provide the title compound as a foam (0.43 g, 56%), $\nu_{max}$ (CH$_2$Cl$_2$) 3400, 1780, 1727, 1685 and 1150 cm$^{-1}$; $\delta_H$ (CDCl$_3$) 1.52 and 1.54 (9H,2s), 1.6–1.8 (1H,m), 2.3–2.7 (3H,m), 3.46, 3.52 and 3.54, 3.62 (2H,2ABq,J=15.2 Hz, 16.8 Hz), 4.28 (1H,br s, exch.), 4.58 (2H,s), 4.9–5.0 (1H,m), 5.07 and 5.16 (1H,2d,J4.8 Hz) 5.29 and 5.39 (1H,br s; s on D$_2$O exch.), 5.45 and 5.54 (1H,2dd,J4.7, 8.5 Hz), 6.8–7.4 (5H,m), 7.40 and 7.59 (1H,2d,J.8.5 Hz); [mass spectrum; +ve ion (3-nitrobenzylalcohol, sodium acetate) MNa+, 531].

d) t-Butyl 2-[4-(5S)-2-oxotetrahydrofuran-5-yl-carbonylmethylthio]-3-phenoxyacetamidoazetidin-2-one-1-yl]-2-tri-n-butylphosphoranylideneacetate Thionyl chloride (0.34 ml, 4.6 mmol) in THF (5 ml) was added dropwise to t-butyl 2(RS)-2-hydroxy-2-[4-(5S)-2-oxotetrahydrofuran-5-ylcarbonylmethylthio)]-3-phenoxyacetamidoazetidin-2-one-1-yl]acetate (1.58 g, 3.1 mmol) and 2,6-lutidine (0.54 ml, 4.6 mmol) in THF (20 ml) at −20° C. The mixture was stirred for 0.5 h without further cooling, the precipitate was filtered off and the filtrate evaporated in vacuo. Toluene was added and the solution reevaporated to provide t-butyl (2RS)-2-chloro-2-[4-[(5S)-2-oxotetrahydrofuran-5-yl-carbonylmethylthio]-3-phenoxyacetamidoazetidin-2-one-1-yl]acetate as a foam (1.81 g) which was used immediately.

Tri-n-butylphosphine (1.7 ml, 6.8 mmol) was added to the chloro compound in dioxan (10 ml), and the reaction mixture was stirred for 0.25 h. It was diluted with ethyl acetate, washed twice with water then with brine, dried, concentrated and flash chromatographed, eluting with 60,75,90 and 100% ethyl aceate in hexane, to give the title compound as a foam (0.84 g,39%), $\nu_{max}$ (CH$_2$Cl$_2$) 3410,1782,1760,1725,1685, 1235 and 1165 cm$^{-1}$; [mass spectrum: +ve ion (thioglycerol) MH+, 693].

(e) t-Butyl (6R,7R)-3-[(5S)-2-oxotetrahydrofuran-5-yl]-7-phenoxyacetamidoceph-3-em-4-carboxylate t-Butyl 2-[4-[(5S)-2-oxotetrahydrofuran-5-yl carbonylmethylthio]-3-phenoxyacetamidoazetidin-2-one-1-yl]-2-tri-n-butylphosphoranylideneacetate (0.84 g) and benzoic acid (20 mg) in toluene (20 ml) were purged with argon then heated in an oil bath at 120° C. for 1 h. The cooled solution was flash chromatographed, eluting with 40,50 and 75% ethyl acetate in hexane, to provide the title compound (0.43 g, 74%), $\nu_{max}$ (CH$_2$Cl$_2$) 3400, 1780, 1727, 1710, 1695, 1515, 1165, 1235, 1172 and 1150 cm$^{-1}$; $\delta_H$ (CDCl$_3$) 1.54 (9H,s), 1.9–2.1 (1H,m), 2.6–2.85 (3H,m), 3.28 and 3.58 (2H,ABq,J18.7 Hz), 4.58 (2H,s), 5.04 (1H,d,J5.1 Hz), 5.6–5.75 (1H,m), 5.97 (1H,dd,J5.0,9.5 Hz), 6.9–7.1 and 7.3–7.4 (5H,m), 7.23 (1H,d,J9.4 Hz); [mass spectrum: +ve ion (3-nitrobenzylalcohol, sodium acetate)MNa+, 497].

Further elution with 75% ethyl acetate in hexane provided t-butyl (6R,7R)-3-[(5R)-2-oxotetrahydrofuran-5-yl]-7-phenoxyacetamidoceph-3-em-4-carboxylate (0.11 g, 19%), $\nu_{max}$ (CHCl$_2$) 3400, 1785, 1720, 1690, 1230, 1145 cm$^{-1}$; $\delta_H$ (250 MHz, CDCl$_3$) 1.55 (9H, s, 2.4–2.8 (4H, m), 3.43 and 3.49 (2H, ABq, J 18.2 Hz), 4.58 (2H, s), 5.02 (1H, d, J 4.9 Hz), 5.8–6.0 (2H m), 6.9–7.4 (6H, m). [Mass spectrum: +ve ion (3-nitrobenzylalcohol, sodium acetate) MNa+, 497].

EXAMPLE 1

Method B

(a) t-Butyl 2-[(3R,4R)-4-(5S)-2-oxotetrahydrofuran-5-ylcarbonylmethylthio]-3-phenoxyacetamidoazetidin-2-on-1-yl]-2-triphenylphosphoranylideneacetate.

t-Butyl (2RS)-2-chloro-2-[(3R,4R)-4-[(5S)-2-oxotetrahydrofuran-5-ylcarbonylmethylthio]-3-phenoxyacetamidoazetidin-2-on-1-yl]acetate, prepared from the hydroxy compound (3.330 g, 6.55 mmol) as described in example 1(d), triphenylphosphine (3.435 g, 13 mmol) and 2,6-lutidine (1.14 ml, 9.8 mmol) in dioxan (10 ml) were stirred for 4 h. diluted with ethyl acetate, washed with water, 5% citric acid solution, water and brine, dried, concentrated and flash chromatography eluting with 50,60,75, 90 and 100% ethyl acetate in hexane to provide the title compound (2.869 g, 58%), $\nu_{max}$(CH$_2$Cl$_2$) 3380, 1785, 1760, 1725, 1683, 1485, 1367, 1218, 1155 cm$^{-1}$; [mass spectrum: +ve ion (3-nitrobenzyl alcohol-sodium acetate) MNa+(775)].

(b) t-Butyl (6R,7R)-3-[(5S)-2-oxotetrahydrofuran-5-yl]-7-phenoxyacetamidoceph-3-em-4-carboxylate.

t-Butyl 2-[(3R,4R)-4-[(5S)-2-oxotetrahydrofuran-5-ylcarbonylmethylthio]-3-phenoxyacetamidoazetidin-2-on-1-yl]-2-triphenylphosphoranylidene acetate (2.869 g) and benzoic acid (20 mg) in toluene (60 ml) were purged with argon then heated in an oil bath at 120° C. for 32 h. The cooled solution was flash chromographed on silica gel eluting with 35,40 and 50% ethyl acetate in hexane to provide the title compounds (5S isomer; 0.373 g, 21%) and (5R isomer; 0.134 g, 7%) both identical with those described in example 1(e) (Method A).

EXAMPLE 2

(a) t-Butyl (6R,7R)-7-amino-3-[(5S)-2-oxo-tetrahydrofuran-5-yl]ceph-3-em-4-carboxylate Phosphorus pentachloride (0.35 g,1.7 mmol) in dichloromethane (9 ml) was added to t-butyl (6R,7R)-3-[(5S)-2-oxotetrahydrofuran-5-yl]-7-phenoxyacetamidoceph-3-em-4-carboxylate (0.526 g, 1.1 mmol) and N-methylmorpholine (0.24 ml, 2.2 mmol) in dichloromethane (15 ml) at <−20° C. The reaction was stirred at −15±5° C. for 0.75 h then methanol (3 ml) was added. Stirring was continued for 0.75 h without further cooling and then water (10 ml) was added and the mixture was stirred vigorously for 1 h. The dichloromethane was removed in vacuo, ethyl acetate (ca 10 ml) added, the mixture adjusted to pH5.5 with dilute ammonium hydroxide solution and extracted twice with ethyl acetate. The extracts were washed with brine, dried, concentrated and flash chromatographed, eluting with 40,50,75% ethyl acetate in hexane, to give the title compound as a foam (0.15 g,40%); (Found: M+, 340.1097. C$_{15}$H$_{20}$N$_2$O$_5$S requires M, 340.1093); $\nu_{max}$ (CH$_2$Cl$_2$) 1770,1710,1362,1350,1235 and 1170 cm$^{-1}$; $\delta_H$ (CDCl$_3$) 1.54 (9H,s), 1.9–2.1 (1H,m), 2.5–2.8 (3H,m), 3.27 and 3.56 (2H,ABq,J18.5 Hz), 4.80 (1H,d,J5Hz), 4.96 (1H,d,J5 Hz), 5.6–5.7 (1H,m).

(b) t-Butyl (6R,7R)-7-[2-(Z)-methoxyimino-2-(2-tritylaminothiazol-4-yl)acetamido]-3-[(5S)-2-oxotetrahydrofuran-5-yl]ceph-3-em-4-carboxylate Methanesulphonyl chloride (23 μl, 0.3 mmol) was added to sodium 2-(Z)-methoxyimino-2-(2-tritylaminothiazol-4-yl)acetate (0.12 g, 0.25 mmol) in DMF (0.5 ml) at −40° C. The mixture was allowed to warm to −10° C. over 0.5 h then cooled to −30° C. and t-butyl (6R,7R)-7-amino-3-[(5S)-2-oxotetrahydrofuran-5-yl]ceph-3-em-4-carboxylate (68 mg, 0.2 mmol) in DMF (1 ml) and pyridine (24 μl, 0.3 mmol) was added. The reaction was stirred for 1 h without cooling, then diluted with ethyl acetate, washed twice with water and brine, dried, concentrated and flash chromatographed, eluting with 40,50% ethyl acetate in hexane, to give the title compound (92 mg, 60%), $\delta_H$ (CDCl$_3$) 1.53 (9H,m), 1.9–2.1 (1H,m), 2.5–2.8 3H,m), 3.27 and 3.57 (2H,ABq,J18.7 Hz), 4.07 (3H,s), 5.06 (1H,d,J5Hz), 5.6–5.8 (1H,m), 5.98 (1H,dd,J5,9 Hz), 6.72 (1H,d,J9 Hz), 6.74 (1H,s), 7.02 (1H,s), 7.2–7.4 (15H,m); [mass spectrum: +ve ion (thioglycerol)MH+, 766].

EXAMPLE 3

Sodium (6R,7R)-7-[2-(2-Aminothiazol-4-yl)-2-(Z)-methoxyiminoacetamido]-3-[(5RS)-2-oxotetrahydrofuran-5-yl]ceph-3-em-4-carboxylate t-Butyl (6R,7R)-7-[2-(Z)-methoxyimino-2-(2-aminothiazol-4-yl)acetamido]-3-[(5S)-2-oxotetrahydrofuran-5-yl]ceph-3-em-4-carboxylate (90 mg) was dissolved in 90% formic acid, stirred 0.5 h then hydrochloric acid (50 μl) was added. The mixture was stirred for an additional 1 h. The precipitate was filtered off, washed with 90% formic acid, and the filtrate evaporated to dryness. Water was added to the residue, the mixture adjusted to pH5 with 0.1M sodium hydroxide, washed with ether and freeze dried.

The crude sodium salt (0.125 g) was HP20SS, eluting with 0,1,2,3% THF in water. Fractions containing, the title compound were combined, concentrated and then freeze dried to give the sodium salt (31 mg, 53%); $\nu_{max}$ (KBr) 1758, 1664, 1608, 1533, 1390, 1183 and 1037 cm$^{-1}$; $\delta_H$ (D$_2$O) 2.0–2.8 (4H,m), 3.37 and 3.63, 3.39 and 3.53 (2H,2ABq,J17.5,17.9 Hz), 3.94 (3H,s), 5.20, 5.22 (1H,2d,J5 Hz), 5.5–5.6 (1H,m), 5.78 (1H,d,J5Hz), 6.98 (1H,s); [mass spectrum: +ve ion (thioglycerol) MH+, 490].

EXAMPLE 4 t-Butyl (6R,7R)-3-[(5S)-2-oxotetrahydrofuran-5-yl]-7-[2-(2-tritylaminothiazol-5-yl)-2-(Z)-trityloxyiminoacetamido]ceph-3-em-4-carboxylate The title compound was prepared from sodium 2-(2-tritylaminothiazol-4-yl)-2-(Z)-trityloxyiminoacetate (0.28 g, 0.4 mmol) using the method described in Example 2b, (0.22 g, 56%); $\delta_H$ (CDCl$_3$) 1.56 (9H,s), 1.7–2.0 (1H,m), 2.5–2.8 (3H,m), 3.09 and 3.50 (2H,ABq,J18.7 Hz), 5.06 (1H,d,J5 Hz), 5.6–5.7 (1H,m), 6.13 (1H,dd,J5, 8.6 Hz), 6.42 (1H,s) 6.77 (1H,s), 7.16 (1H,d,J8.6 Hz), 7.2–7.5 (30H,m); [mass spectrum: +ve ion (thioglycerol) MH+, 994].

EXAMPLE 5

(6R,7R)-7-[2-(2-Aminothiazol-4-yl)-2-(Z)-hydroxyiminoacetamido]-3-[(5RS)-2-oxotetrahydrofuran-5-yl)ceph-3-em-4-carboxylic acid t-Butyl (6R,7R)-3-[(5S)-2-oxotetrahydrofuran-5-yl]-7-[2-(2-tritylaminothiazol-4-yl)-2-(Z)-trityloxyiminoacetamido]ceph-3-em-4-carboxylate (0.22 g) was dissolved in 0.1M hydrochloric acid in 90% formic acid (2.5 ml) and stirred for 1 h. Concentrated hydrochloric acid (0.1 ml) was added and stirring was continued for a further 0.5 h. The precipitate was filtered off, washed with 90% formic acid, and the filtrate was evaporated to dryness. The residue in water was adjusted to pH3 with solid potassium carbonate, washed with ether and freeze dried. The crude product (0.153 g) was chromatographed on HP20SS, eluting with 0,2,4,6% THF in water. Fractions containing the title compound were combined, concentrated and freeze dried (41 mg, 40%), $\nu_{max}$ (KBr) 1764, 1664, 1609, 1529, 1389 and 1184 cm$^{-1}$; $\delta_H$ (D$_2$O) 2.1–2.8 (4H,m , 3.37 and 3.63, 3.39 and 3.53 (2H,2ABq,J17.5,17.8 Hz), 5.21, 5.23 (1H,2d, J4.6 Hz), 5.5–5.65 (1H,m), 5.82 (1H,d,J4.6 Hz), 6.95 (1H,s); [mass spectrum: +ve ion (thioglyerol) MH+, 454].

EXAMPLE 6

(a) (RS)-2-Oxotetrahydrofuran-4-ylcarboxylic acid

Sodium aconate (4.25g) (N. R. Campbell and J. H. Hunt, J. Chem. Soc., 1947, 1176) in water (100 ml) was hydrogenated in the presence of 10% palladium on carbon (0.2 g). After removal of the catalyst the aqueous solution was passed through a column of 'Amberlite' IR120(H+) ion exchanged resin then concentrated in vacuo. The residue in dichloromethane was dried (MgSO$_4$) and evaporated to provide the title compound (2.76 g, 75%), $\nu_{max}$ (CH$_2$Cl$_2$) 1785, 1755, 1720, 1170 cm$^{-1}$; $\delta_H$ (90 MHz, (CD$_3$)$_2$CO) 2.74 (2H, d, J8 Hz), 3.35–3.75 (1H, m), 4.3–4.65 (2H, m), 7.51 (1H, bs).

(b) (RS)-4-Chloroacetyltetrahydrofuran-2-one

Oxalyl chloride (2.6 ml, 30 mmol) and DMF (1 drop) were added to (RS)-2-oxotetrahydrofuran-4-ylcarboxylic acid (2.76 g, 21 mmol) in dichloromethane (25 ml) and the mixture stirred 0.5 h, then evaporated in vacuo. Toluene was added to the residue then reevaporated to leave the acid chloride, $\nu_{max}$ (CH$_2$Cl$_2$) 1790 cm$^{-1}$.

The acid chloride in ether (50 ml) was added dropwise to an ice bath cooled solution of diazomethane (45 mmol) in ether (120 ml). The solution was stirred 0.5 h then a stream of hydrogen chloride gas passed into it for 5 minutes. The mixture was stirred 0.25 h then washed twice with brine, dried and evaporated to an oil (1.635 g). The brine washings were extracted with ethyl acetate (×2), dried and evaporated to give more crude product (2.015 g). The combined crude product was flash chromatographed on silica gel eluting with 30, 40% ethyl acetate in hexane (2.737 g, 79%), 6H (90 MHz, CDCl$_3$) 2.74 (2H d, J8 Hz), 3.6–4.1 (1H, m), 4.1–4.65 (4H, m).

(c) t-Butyl (2RS)-2-hydroxy-2-[(3R,4R)-4-[(4RS)-2-oxotetrahydrofuran-4-ylcarbonylmethylthio]-3-phenoxyacetamidoazetidin-2-on-1-yl]acetate (RS)-4-Chloroacetyltetrahydrofuran-2-one (2.060 g, 12.6 mmol), followed by potassium carbonate (0.690 g, 5 mmol) were added to crude t-butyl (2RS)-2-hydroxy-

[(3R,4R)-4-mercapto-3-phenoxyacetamidoazetidin-2-on-1-yl]acetate (3.866 g) (prepared as described in Example 1c) in acetone (10 ml). The reaction was stirred 1 h. then diluted with ethyl acetate, washed with water (x2) and brine, dried, concentrated and flash chromatographed on silica gel eluting with 50,60,75,90% ethyl acetate in hexane to provide the title compound as a foam (3.458 g, 68%), $v_{max}$ (CH$_2$Cl$_2$) 3380, 1780, 1680, 1235, 1150 cm$^{-1}$; [Mass spectrum: +ve ion (thioglycerol) MH+ (509)].

(d) t-Butyl 2-[(3R,4R)-4-[(4RS)-2-oxotetrahydrofuran-4-ylcarbonylmethylthio]-3-phenoxyacetamidoazetidin-2-on-1-yl]-2-triphenylphosphoranylideneacetate Thionyl chloride (0.75 ml, 10.2 mmol) in THF (5 ml) was added dropwise to the hydroxy compound (3.458 g, 6.8 mmol) and 2,6-lutidine (1.2 ml, 10.2 mmol) in THF (15 ml) at < −15° C. The reaction mixture was stirred 0.5 h, filtered and the filtrate evaporated in vacuo. Toluene was added then reevaporated to give crude t-butyl (2RS)-2-chloro-2-[(3R,4R)-4-[(4RS)-2-oxotetrahydrofuran-4-ylcarbonylmethyltho]-3-phenoxyacetamidoazetidin-2-on-1-yl]acetate as a foam (3.946 g), which was in the next step at once.

Triphenylphosphine (3.560 g, 13.6 mmol) and 2,6-lutidine (1.2 ml, 10.2 mmol) were added to the crude chloro compound in dioxan (20 ml). The mixture was stirred 3 h, diluted with ethyl acetate, washed successively with water, 5% citric acid, water and brine, dried, concentrated and flash chromatographed on silica gel eluting with 50,60,75,90,100% ethyl acetate in hexane to provide the title compound (3.121 g, 61%); [Mass spectrum; +ve ion (3-nitrobenzyl alcohol, sodium acetate) MNa+ (775)].

(e) t-Butyl (6R,7R)-3-(4RS)-2-oxotetrahydrofuran-4-yl[-7-phenoxyacetamidoceph-3-em-4-carboxylate The phosphorane from Example 6d (3.121 g) and benzoic acid (20 mg) in xylene (60 ml) were purged with argon then heated at 120° C. for 24 h. The cooled solution was flash chromatographed on silica gel eluting with 35% ethyl acetate in hexane to give the title compound as a foam (0.433 g, 22%), $v_{max}$ (CH$_2$Cl$_2$) 3395, 1780, 1715, 1695, 1230, 1165 cm$^{-1}$; $\delta_H$ (250 MHz, CDCl$_3$) 1.55 (9H, s), 2.35–3.0 (2H, m), 3.21 and 3.46, 3.26 and 3.50 (2H, 2ABq, J 17.8 Hz), 4.0–4.7 (3H, m), 4.56 (2H, s), 5.01, 5.03 (1H, 2d, J 4.9 Hz), 5.91, 5.94 (1H, 2dd, J 4.9, 9.2 Hz), 6.9–7.4 (6H, m); [Mass spectrum: +ve ion (3-nitrobenzyl alcohol-sodium acetate) MNa+ (497)].

EXAMPLE 7

(a) t-Butyl (6R,7R)-7-amino-3-[(4RS)-2-oxotetrahydrofuran-4-yl]ceph-3-em-4-carboxylate A solution of phosphorous pentachloride (0.380 g, 1.8 mmol) in dichloromethane (9.5 ml) was added to t-butyl (6R,7R)-3-[(4RS)-2-oxotetrahydrofuran-4-yl]-7-phenoxyacetamidoceph-3-em-4-carboxylate (0.554 g, 1.2 mmol) and N-methylmorpholine (265 μh, 2.4 mmol) in dichloromethane (15 ml) at < −20° C. under argon. Stirred 0.5 h at −15°±5° C. then methanol (3.5 ml) added, stirred 0.75 h then water (10 ml) added and stirred vigorously 1 h. The dichloromethane was removed in vacuo. ethyl acetate added and the aqueous layer adjusted to pH7 with dilute ammonium hydroxide and extracted twice with ethyl acetate. The extracts were washed with brine, dried, concentrated and flash chromatographed on silica gel eluting with 40,50,60,70,75% ethyl acetate in hexane to provide the title compound as a foam (0.120 g, 29%): (Found: M+, 340.1113. C$_{15}$H$_{20}$N$_2$O$_5$S requires M, 340.1093); $v_{max}$ (CH$_2$Cl$_2$) 1775, 1715, 1367, 1155 cm$^{-1}$; $\delta_H$ (250 MHz, CDCl$_3$) 1.54 (9H, s), 1.97 (2H, bs), 2.35–2.95 (2H, m), 3.26 and 3.49 3.28 and 3.49 (2H, 2ABq, J 17.7 Hz), 4.0–4.45 (3H, m), 4.77, 4.79 (1H, 2d, J 4.7 Hz), 4.93, 4.95 (1H, 2d, J 4.7 Hz).

(b) t-Butyl (6R,7R)-7-[2-(Z)-methoxyimino-2-(2-trityl-aminothiazol-4-yl)acetamido]-3-[(4RS)-2-oxotetrahydrofuran-4-yl]ceph-3-em-4-carboxylate Mesyl chloride (39 μl, 0.5 mmol) was added to 2-(Z)-methoxyimino-2-(2-tritylaminothiazol-4-yl)acetic acid hydrochloride (0.215 g, 0.45 mmol) and N,N-diisopropylethylamine (157 μl, 0.9 mmol) in DMF at −40° C. Stirred 0.5 h at −35°±5° C. then t-butyl (6R,7R)-7-amino-3-[(4RS)-2-oxotetrahydrofuran-4-yl]ceph-3-em-4-carboxylate (0.120 g, 0.35 mmol) in DMF (2 ml) followed by pyridine (41 ul, 0.5 mmol) were added. Stirred 1 h. without further cooling then diluted with ethyl acetate, washed twice with water and with brine, dried, concentrated then flash chromatographed on silica gel eluting with 30, 35, 40, 50% ethyl acetate in hexane to give the title compound as a foam (0.167 g, 62%), $v_{max}$ (CHCl$_2$) 3390, 1775, 1715, 1670, 1515, 1150 cm$^{-1}$; $\delta_H$ (250 MHz, CDCl$_3$) 1.53, 1.60 (9H, 2s), 2.35–2.65 (2H, m), 3.24 and 3.51, 3.26 and 3.51 (2H, 2ABq, J 18.0 Hz), 4.0–4.5 (3H, m), 4.07 (3H, s), 5.03, 5.05 (1H, 2d, J 4.9Hz), 5.92, 5.95 (1H, 2dd, J 4.9, 8.8 Hz), 6.73 (1H, s), 6.76 (1H, d, J 8.9 Hz), 7.00 (1H, s), 7.30 (15H, s). [Mass spectrum: +ve ion (3-nitrobenzyl alcohol-sodium acetate) MNa+ (788)].

EXAMPLE 8

Sodium (6R,7R)-7-2-aminothiazol-4-yl)-2-(Z)-methoxyiminoacetamido]-3-[(4RS)-2-oxotetrahydrofuran-4-yl]ceph-3-em-4-carboxylate t-Butyl (6R,7R)-7-[2-(Z)-methoxyimino-2-(2-tritylaminothiazol-4-yl)acetamido]-3-[(4RS)-2-oxotetrahydrofuran-4-yl]ceph-3-em-4-carboxylate (0.167 g, 0.22 mmol) was dissolved in 0.1M HCl in 90% formic acid (2.2 ml), set aside for 0.75 h, conc. hydrochloric acid (50 μl) added and left for a further 1 h. The mixture was evaporated in vacuo, diluted with water, adjusted to pH6 with 0.1M sodium hydroxide then chromatographed on HP20SS eluting with 0,1,2% THF in water. Fractions containing the title compound (HPLC) were concentrated in vacuo and freeze dried (72.5 mg, 68%), $v_{max}$ (KBr) 1757, 1664, 1604, 1529, 1388, 1182, 1036 cm$^{-1}$; $\delta_H$ (250 MHz, D$_2$O) 2.6–2.9 (2H, m), 3.35 and 3.63 (2H, ABq, J 17.5 Hz), 3.8–4.05 (1H, m), 3.96 (3H, s), 4.15–4.6 (2H, m), 5.18, 5.19 (1H, 2d, J 4.5Hz , 5.75, 5.76 (1H, 2d, J 4.5 Hz), 6.99 (1H, s). [Mass spectrum: +ve ion (thioglycerol) MH+ (490), MNa+ (512)].

EXAMPLE 9 t-Butyl (6R,7R)-7-2-(Z)-t-butoxycarbonylmethoxyimino-2-(2-tritylaminothiazol-4-yl)acetamido]-3-[(5S)-2-oxotetrahydrofuran-5-yl]ceph-3-em-4-carboxylate.

Mesyl chloride (43 μl, 0.55 mmol) was added to 2(Z)-t-butoxycarbonylmethoxyimino-2-(2-tritylaminothiazol-4-yl)acetic acid (DE 2,812,625) (0.272 g, 0.5 mmol) and N,N-diisopropylethylamine (87 μl, 0.5mmol) in DMF (1 ml) at < −45° C. After 0.5 h at −30°±20° C., t-butyl (6R,7R)-7-amino-3-[(5S)-2-oxotetrahydrofuran-5-yl]ceph-3-em-4-carboxylate (0.170 g, 0.5 mmol) in DMF (2 ml) followed by pyridine (45μl, 0.55 ml), were added. Stirred 1 h without further cooling then diluted with ethyl acetate, washed twice with water and with brine, dried, concentrated and flash chromatographed on silica gel eluting with 25,30,35,40,50% ethyl acetate in hexane to give the title compound as a foam (0.290 g, 53%), $v_{max}(CH_2Cl_2)$ 3390, 1780, 1725, 1685, 1522, 1365, 1240, 1043 cm$^{-1}$; $\delta_H$(90 MHz, CDCl$_3$) 1.40 (9H, s), 1.51 (9H, s), 1.6-2.7 (4H, m), 3.22 and 3.50 (2H, ABq, J 19 Hz), 4 72 (2H, s), 5.02 (1H, d, J 5 Hz), 5.5-5.75 (1H, m), 5.92 (1H, dd, J 5, 9 Hz), 6.78 (1H, s), 6.96 (1H, s), 7.27 (15H, s), 8.47 (1H, d, J 9Hz); [mass spectrum: +ve ion (3-nitrobenzyl alcohol-sodium acetate)MNa+, 888].

EXAMPLE 10

Disodium (6R,7R)-7-2-(2-aminothiazol-4-yl)-2-(Z)-carboxymethoxyiminoacetamido]-3-[(5RS)-2-oxotetrahydrofuran-5-yl]ceph-3-em-4-carboxylate.

t-Butyl (6R,7R)-7-[2-(Z)-t-butoxycarbonylmethoxyimino-2-(2-tritylaminothiazol-4-yl)acetamido]-3-[(5S)-2-oxo-tetrahydrofuran-5-yl]ceph-3-em-4-carboxylate (0.290 g, 0.33 mmol) was dissolved in 0.1M HCl in 90% formic acid (3.3 ml). After 0.5 h conc. HCl (75 μl) was added and the mixture set aside for 1.5 h then evaporated to dryness. Water was added to the residue, adjusted to pH6 with 0.5M sodium hydroxide then chromatographed on HP20SS eluting with water. Fractions containing the title compound (HPLC) were combined, concentrated and freeze dried (105 mg, 56%), $v_{max}$ (KBr) 3411, 1757, 1660, 1603, 1532, 1399, 1320, 1184, 1039 cm$^{-1}$; $\delta_H$(250 MHz, (CD$_3$)$_2$SO) 1.9-2.7 (4H, m), 3.12 and 3.45, 3.28 and 3.34 (together 2H, 2ABq, J 17, 17.5 Hz), 4.23, 4.27 (together 2H, 2s), 5.01 (1H, d, J 5Hz), 5.6-6.0 (2H, m), 6.83, 6.84 (together 1H, 2s), 6.41 (2H, s); [mass Spectrum: +ve ion (thioglycerol) MH+ (556), MNa+ (578)].

EXAMPLE 11

Pivaloyloxymethyl (6R,7R)-7-[2-(2-aminothiazol-4-yl)-2-(Z)-methoxyiminoacetamido]-3-[(5RS)-2-oxotetrahydrofuran-5-yl]ceph-3-em-4-carboxylate.

Pivaloyloxymethyl bromide (0.10 g, ca. 0.5 mmol) and sodium iodide (0.1 g) in acetone (1 ml) were stirred for 0.25 h, filtered and evaporated in vacuo. The iodide in toluene (0.5 ml) was added to sodium (6R,7R)-7-[2(2-aminothiazol-4-yl)-2-(Z)-methoxyiminoacetamido]-3-[(5RS)-2-oxotetrahydrofuran-5-yl]ceph-3-em-4-carboxylate (0.124 g, 0.25 mmol) in N-methylpyrrolidone (2 ml) and stirred for 0.5 h. The reaction mixture was diluted with ethyl acetate, washed twice with water, and with brine, dried, concentrated and flash chromatographed on silica gel eluting with 80,90,100% ethyl acetate in hexane to give the title compound (86 mg, 59%), $v_{max}(CH_2Cl_2)$ 1780, 1753, 1735, 1682, 1532, 1374, 1121, 1046 cm$^{-1}$; $\delta_H$(250 MHz, CDCl$_3$) (9H, s), 1.9-2.2 (1H, m), 2.4-2.8 (3H, m), 3.34 and 3.64, 3.48 and 3.59 (together 2H, 2ABq, J 18.9, 18.4 Hz), 4.08 (3H, s), 5.10, 5.11 (together 1H, 2d, J 4.9 Hz), 5.35 (2H, bs), 5.5-5.95 (3H, m), 6.00, 6.10 (together 1H, 2dd, J 9, 4.9 Hz), 6.85, 6.87 (together 1H, 2s), 7.52, 7.54 (together 1H, 2d, J 9 Hz); [mass spectrum: +ve ion (3-nitrobenzyl alcohol-sodium acetate) MH+(582) MNa+(604)].

EXAMPLE 12

(a) (RS)-3-Bromoacetyltetrahydrofuran-2-one

Oxalyl chloride (6.4 ml, 74 mmol) and DMF (1 drop) were added to (RS)-2-oxotetrahydrofuran-3-ylcarboxylic acid (T.N. Rozanova and I.T. Strukov, Khim.-Farm. Zh., 2, 20, 1968) (6.10 g, 49 mmol) in dichloromethane (50 ml) and the mixture stirred 1h, then evaporated in vacuo, redissolved in dichloromethane and reevaported to give the acid chloride, $v_{max}(CH_2Cl_2)$ 1779 cm$^{-1}$.

The acid chloride in ether (50 ml) was added dropwise to an ice bath cooled solution of diazomethane (100 mmol) in ether (200 ml), stirred for 0.25 h, then evaporated to give the diazoketone as a dark oil, $v_{max}(CH_2Cl_2)$ 2114, 1770, 1742, 1644, 1363 cm$^{-1}$.

The diazoketone in dichloromethane (50 ml) was cooled in an ice bath, 48% hydrobromic acid (9.2 ml, 54 mmol) added, stirred 0.25 h, washed with water, dried concentrated and flash chromatographed on silica gel eluting with 10,12.5 and 15% ethyl acetate in hexane to provide the title compound (3.988 g, 39%), $v_{max}(CH_2Cl_2)$ 1770, 1740, 1724, 1659, 1376, 1270, 1169 cm$^{-1}$; $\delta_H$(90 MHz, CDCl$_3$) 2.1-3.1 (2H, m), 3.7-4.6 (5H, m); [mass spectrum: +ve ion (ammonia) MNH$_4$+ (224)].

(b) t-Butyl (2RS)-2-hydroxy-2-[(3R,4R)-4-[(3RS)-2-oxotetrahydrofuran-3-ylcarbonylmethylthio]-3-phenoxyacetamidoazetidin-2-on-1-yl]acetate.

The title compound was prepared by the method described in Example 1c but using 3-bromoacetyltetrahydrofuran-2-one, (64%), $v_{max}(CH_2Cl_2)$ 3488, 3406, 1782, 1733, 1695, 1520, 1496, 1372 cm$^{-1}$; $\delta_H$(250 MHz, CDCl$_3$) 1.52 (9H, m), 2.2-2.5 (1H, m), 2.7-2.9 (1H, m), 3.5-4.5 (5H, m), 4.59 (2H, s), 4.95-5.6 (4H, m) 6.9-7.6 (6H, m); [mass spectrum: +ve ion (thioglycerol) M-H (507)].

(c) t-Butyl (2RS)-2-[(3R,4R)-4-[(3RS)-2-oxotetrahydrofuran-3-ylcarbonylmethylthio]-3-phenoxyacetamidoazetidin-2-on-1-yl]-2-tri-n-butylphosphoranylideneacetate Prepared using the method described in Example 1(d) except that the product in ethyl acetate was first washed with dilute sodium hydrogen carbonate solution. The title compound was obtained as a foam (72%), $v_{max}(CH_2Cl_2)$ 3416, 1766, 1731, 1714, 1690, 1628, 1601, 1522, 1495, 1172 cm$^{-1}$; [mass spectrum: +ve ion (3-nitrobenzyl alcohol-sodium acetate) MNa+ (715)].

(d) t-Butyl (6R,7R)-3-(3R or 3S)-2-oxotetrahydrofuran-3-yl]-7-phenoxyacetamidoceph-3-em-4-carboxylate

Method A t-Butyl (2RS)-2-[(3R,4R)-4-[(3RS)-2-oxotetrahydrofuran-3-ylcarbonylmethylthio]-3-phenoxyacetamidoazetidin-2-on-1-yl]-2-tri-n-butylphosphoranylideneacetate (7.457 g) and benzoic acid (50 mg) in toluene (150ml) were purged with argon then heated in an oil bath at 120° C. for 24 h. The solution was concentrated and flash chromatographed on silica gel eluting with 25,30,35 and 40% ethyl acetate in hexane to provide the title compound (0.390 g, 8%), $\nu_{max}$(CH$_2$Cl$_2$) 3406, 1788, 1773, 1712, 1698, 1519, 1370, 1152 cm$^{-1}$; $\delta_H$(250 MHz, CDCl$_3$) 1.54 (9H, s), 2.15-2.35 (1H, m), 2.65-2.8 (1H, m), 3.06 and 3.82 (2H, ABq, J 18.3 Hz), 4.35-4.55 (3H, m), 4.57 (2H, s), 5.09 (1H, d, J 5Hz), 5.95 (1H, dd, J 5,9 Hz), 6.9-7.4 (6H, m); [mass spectrum: +ve ion (3-nitrobenzyl alcohol-sodium acetate) MNa$^+$ (497)]. Also obtained in later fractions were inter alia: t-butyl (6R,7R)-3-[(3RS)-2-oxotetrahydrofuran-3-yl]-7-phenoxyacetamidoceph-2-em-4-carboxylate (0.663 g, 13%); $\nu_{max}$(CH$_2$Cl$_2$) 3405, 1779, 1738, 1696 cm$^{-1}$; $\delta_H$ (250 MHz, CDCl$_3$) inter alia 4.83, 5.17 (together 1H, 2bs), 6.19, 6.38 (together 1H, 2bs); [mass spectrum: +ve ion (thioglycerol) MH$^+$ (475)]; and t-butyl (6R,7R)-3-[(3S or 3R)-2-oxotetrahydrofuran-3-yl]-7-phenoxyacetamidoceph-3-em-4-carboxylate (0.138 g), 3%); $\nu_{max}$(CH$_2$Cl$_2$) 3404, 1786, 1773, 1716, 1697 cm$^{-1}$; $\delta_H$(250 MHz, CDCl$_3$) inter alia 2.4-2.6 (2H, m), 3.26 and 3.59 (2H, ABq, J 18.1 Hz), 3.83 (1H, dd, J 9.4, 11.9 Hz), 4.2-4.6 (2H, m), 4.57 (2H, s), 5.06 (1H, d, J 4.9 Hz), 5.92 (1H, dd, J 4.9, 9.4Hz); [mass spectrum: +ve ion (3-nitrobenzyl alcohol-sodium acetate) MNa$^+$ (497)].

Method B

Phosphorus trichloride (85 µl, 1.06 mmol) was added to t-butyl (6R,7R)-3-[(3R or 3S)-2-oxotetrahydrofuran-3-yl]-7-phenoxyacetamidoceph-3-em-4-carboxylate-1-oxide (0.260 g, 0.53 mmol) in DMF (2ml) at −25° C. The mixture was stirred for 10 minutes, ice and ethyl acetate added, washed twice with water then brine, dried concentrated and flash chromatographed eluting with 35% ethyl acetate in hexane to give the title compound (0.115 g, 46%), identical with the material described in Method A.

EXAMPLE 13 t-Butyl (6R,7R)-3-[(3R or 3S)-2-oxotetrahydrofuran-3-yl]-7-phenoxyacetamidoceph-3-em-4-carboxylate-1-oxide t-Butyl (6R,7R)-3-[(3RS)-2-oxotetrahydrofuran-3-yl]-7-phenoxyacetamidoceph-2-em-4-carboxylate (0.663 g, 1.4 mmol) and 55% 3-chloroperoxybenzoic acid (0.430 g, 1.4 mmol) in dichloromethane (10 ml) were stirred for for 10 minutes, washed with dilute sodium metabisulphate solution and dilute sodium hydrogen carbonate, dried concentrated and flash chromatographed on silica gel eluting with 40,50,60% ethyl acetate in hexane to give the title compound (0.269 g, 39%), $\nu_{max}$(CH$_2$Cl$_2$) 3383, 1801, 1771, 1752, 1716, 1698, 1519, 1495, 1370, 1152 cm$^{-1}$; $\delta_H$(250 MHz, CDCl$_3$) 1.59 (9H, s), 2.1-2.3 (1H, m), 2.65-2.85 (1H, m), 3.77 (2H, bs), 4.25-4.6 (4H, m), 4.59 (2H, s), 6.18 (1H, dd, J 10.4, 4.8 Hz), 6.9-7.4 (5H, m), 7.86 (1H, d, J 10.4 Hz). Further elution with ethyl acetate gave t-butyl (6R,7R)-3-[(3S or 3R)-2-oxotetrahydrofuran-3-yl]-7-phenoxyacetamidoceph-3-em-4-carboxylate-1-oxide (0.150 g, 22%), $\nu_{max}$(CH$_2$Cl$_2$) 3380, 1800, 1774, 1719, 1698, 1519, 1495, 1370, 1154 cm$^{-1}$; $\delta_H$(250 MHz, CDCl$_3$) 1.54 (9H, s), 2.45-2.65 (2H, m), 3.33 and 3.65 (2H, ABq, J 18.5 Hz), 4.2-4.65 (5H, m), 6.17 (1H, dd, J 4.8, 10.4 Hz), 6.9-7.4 (5H, m), 7.89 (1H, d, J 10.4 Hz).

EXAMPLE 14

(a) t-Butyl (6R,7R)-7-amino-3-[(3R or 3S)-2-oxotetrahydrofuran-3-yl]ceph-3-em-4-carboxylate Prepared from t-butyl (6R,7R)-3-[(3R or 3S)-2-oxotetrahydrofuran-3-yl]-7-phenoxyacetamidoceph-3-em-4-carboxylate using the method described in Example 2(a), (44%), (Found: M$^+$, 340.1084. C$_{15}$H$_{20}$N$_2$O$_5$S requires M, 340.1093); $\nu_{max}$(CH$_2$Cl$_2$) 1772, 1713, 1370, 1154 cm$^{-1}$; $\delta_H$(250 MHz, CDCl$_3$) 1.53 (9H, s), 1.63 (2H, bs, exch.), 2.1-2.4 (1H, m), 2.6-2.8 (1H, m), 3.05 and 3.80 (2H, ABq, J 18.2 Hz), 4.25-4.55 (3H, m), 4.77 (1H, d, J 5Hz), 5.00 (1H, d, J 5 Hz).

(b) t-Butyl (6R,7R)-7-[2-(Z)-methoxyimino-2-(2-tritylaminothiazol-4-yl)acetamido]-3-[3R or 3S)-2-oxotetrahydrofuran-3-yl]ceph-3-em-4-carboxylate Prepared by the method described in Example 7(b), (87%), $\nu_{max}$(CHCl$_3$) 3397, 1771, 1733, 1690, 1525, 1248, 1046 cm$^{-1}$, $\delta_H$(250 MHz, CDCl$_3$) 1.53 (9H, s), 2.1-2.35 (1H, m), 2.65-2.8 (1H m), 3.05 and 3.82 (2H, ABq, J 18.4 Hz), 4.07 (3H, s), 4.25-4.55 (3H, m), 5.11 (1H, d, J 4.9 Hz), 5.97 (1H, dd, J 8.9, 4.9 Hz), 6.69 (1H, d, J 9.1 Hz), 6.74 (1H, s), 7.00 (1H, s), 7.30 (15H, s); [mass spectrum: +ve ion (3-nitrobenzyl alcohol-sodium acetate) MNa$^+$ (788)].

EXAMPLE 15

Sodium (6R,7R)-7-[2-(2-aminothiazol-4-yl)-2-(Z)-methoxyiminoacetamido]-3-[(3RS)-2-oxotetrahydrofuran-3-yl]ceph-3-em-4-carboxylate Prepared using the method described in Example 8, (74%), $\nu_{max}$(KBr) 1753, 1672, 1604, 1529, 1377, 1037 cm$^{-1}$; $\delta_H$(250 MHz, (CD$_3$)$_2$SO) 2.1-2.5 (2H, m), 3.00 and 3.43, 3.18 and 3.36 (together 2H, 2ABq, J 16.6, 17.1 Hz), 3.83 (3H, s), 4.1-4.4 (2H, m), 4.5-4.7, 5.1-5.3 (together 1H, m), 5.00, 5.03 (together 1H, 2d, J 4.7 Hz), 5.51, 5.57 (together 1H, 2dd, J 4.7, 8.2 Hz), 6.74, 6.77 (together 1H, 2s), 9.50, 9.55 (together 1H, 2d, J 8.2Hz); [mass spectrum: +ve ion (thioglycerol) MH$^+$ (490), MNa$^+$ (512)]

| | In Vitro Biological Data MIC (µg/ml) | |
|---|---|---|
| | Organism | |
| Example No. | E. coli (NCTC 10418) | S. aureus (Oxford) |
| 3 | <0.03 | 1.0 |
| 5 | <0.03 | 0.25 |
| 8 | 32.0 | 4.0 |
| 10 | 0.12 | 8.0 |
| 15 | 0.25 | 4.0 |

We claim:

1. A compound of formula (I) or a salt thereof:

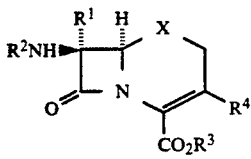 (I)

wherein
$R^1$ is hydrogen, methoxy or formamido;
$R^2$ is acyl selected from the group consisting of

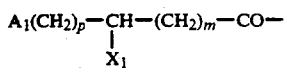 (a)

$A_2CO—$ (b)

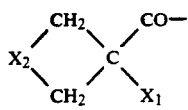 (c)

$A_2—X_3—(CH_2)_p—CO—$ (d)

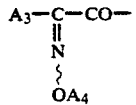 (e)

and

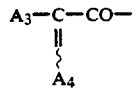 (f)

wherein
p is 0, 1 or 2;
m is 0, 1 or 2;
$A_1$ is $C_{1-6}$ alkyl; $C_{3-6}$ cycloalkyl; cyclohexenyl; cyclohexadienyl; phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{1-6}$ alkylcarbonyloxy; $C_{(1-6)}$alkoxycarbonyl; formyl; $C_{(1-6)}$alkylcarbonyl; ($C_{1-6}$)alkylthio and ($C_{1-6}$)alkyloxy;
$X_1$ is hydrogen; halogen; carboxylic acid; carboxylic ester; sulphonic acid; azido; tetrazolyl; hydroxy; acyloxy; amino; ureido; acylamino; heterocyclylamino; guanidino or acylureido;
$A_2$ is phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; $C_{1-6}$ alkylcarbonyl; and dithietane;
$X_2$ is $CH_2OCH_2$; $CH_2SCH_2$ or alkylene;
$X_3$ is oxygen or sulphur;
$A_3$ is phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; and $C_{(1-6)}$alkylcarbonyl;

$A_4$ is hydrogen; $C_{1-6}$alkyl; $C_{3-8}$cycloalkyl; ($C_{1-6}$)alkoxycarbonyl($C_{1-6}$)alkyl; phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; $C_{(1-6)}$alkylcarbonyl; $C_{2-6}$ alkenyl; carboxy($C_{1-6}$)alkyl; $C_{2-6}$ alkynl; aryl($C_{1-6}$)alkyl; and other acyl groups found in the 7-position of antibacterially active cephalosporins; $CO_2R^3$ is carboxy; carboxylate anion; or $R^3$ is a readily removable carboxy protecting group; $R_4$ is a $\nu$-lactone ring optionally containing an endocyclic double bond, which ring is optionally substituted at any carbon atom by $C_1-C_6$ alkyl; $C_1-C_6$ dialkylamino; alkoxy; hydroxy; halogen; phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; and $C_{(1-6)}$ alkylcarbonyl; or is optionally di-substituted at two adjacent carbon atoms, which are available for substitution, to form an aromatic fused bicyclic system wherein at least one ring is a 5-membered lactone ring and X is sulphur.

2. The compound according to claim 1 wherein
$A_1$ is selected from the group consisting of phenyl, substituted phenyl, thienyl, pyridyl and thiazolyl;
$A_2$ is selected from the group consisting of phenyl; 2,6-dimethoxyphenyl; 2-alkoxy-1-naphthyl; 3-arylisoxazolyl and 3-aryl-5-methyl isoxazolyl, wherein said aryl is phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; and $C_{(1-6)}$alkylcarbonyl; and
$A_3$ is selected from the group consisting of phenyl, substituted phenyl, and aminothiazolyl wherein the amino group may be substituted.

3. The compound according to claim 1 in which $R^2$ is an acyl group of formula (e):

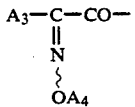 (e)

wherein
$A_3$ is phenyl, substituted phenyl, or aminothiazolyl in which the amino group is optionally protected;
$A_4$ is hydrogen; $C_{1-6}$ alkyl; $C_{3-8}$ cycloalkyl; ($C_{1-6}$)alkoxycarbonyl($C_{1-6}$)alkyl; $C_{2-6}$ alkenyl; carboxy($C_{1-6}$)alkyl, $C_{2-6}$ alkynyl; aryl or aryl($C_{1-6}$)alkyl wherein said aryl is phenyl or naphthyl, each optionally substituted with up to five substituents selected from the group consisting of halogen; mercapto; $C_{1-6}$ alkyl; phenyl; $C_{1-6}$ alkoxy; hydroxy($C_{1-6}$)alkyl; mercapto($C_{1-6}$)alkyl; halo($C_{1-6}$)alkyl; hydroxy; amino; nitro; carboxy; $C_{(1-6)}$alkylcarbonyloxy; $C_{(1-6)}$alkoxycarbonyl; formyl; and $C_{(1-6)}$alkylcarbonyl.

4. A compound according to claim 1 in which $R^1$ is hydrogen.

5. A compound according to claim 2, wherein $A_3$ is 2-aminothiazol-4-yl or 2-tritylaminothiazol-4-yl and $A_4$ is hydrogen, methyl, triphenylmethyl, t-butoxycarbonylmethyl or carboxymethyl.

6. A compound according to claim 1 in which $CO_2R^3$ is carboxy or a carboxylate anion, or $R^3$ is tert-butyl or pivaloyloxymethyl.

7. A compound according to claim 1 in which $R^4$ is 2-oxotetrahydrofuran-5-yl, 2-oxotetrahydrofuran-4-yl or 2-oxotetrahydrofuran-3-yl.

8. A compound according to claim 1 in which X is S or SO.

9. A compound according to claim 1 in which $R^1$ is hydrogen; $R^2$ is 2-(2-aminothiazol-4-yl)-2-(Z)-methoxyiminoacetyl, 2-(2-aminothiazol-4-yl)-2-(Z)-hydroxyiminoacetyl or 2-(2-aminothiazol-4-yl)-2-(Z)-carboxymethoxyiminoacetyl; $CO_2R^3$ is carboxy or a carboxylate anion, or $R^3$ is pivaloyloxymethyl; $R^4$ is 2-oxotetrahydrofuran-5-yl, 2-oxotetrahydrofuran-4-yl or 2-oxotetrahydrofuran-3-yl; and X is sulphur.

10. A compound of formula (Ia) or a pharmaceutically acceptable salt or pharmaceutically acceptable in vivo hydrolysable ester thereof:

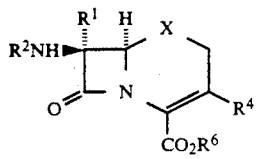
(Ia)

wherein $R^1$, $R^2$, $R^4$ and X are as defined with respect to formula (I) in claim 1 and $CO_2R^6$ is a carboxy group or a carboxylate anion.

11. A compound of formula (Ia) or a pharmaceutically acceptable salt or in vivo hydrolysable ester thereof as defined in claim 10, selected from the group comprising:
(6R,7R)-7-[2-aminothiazol-4-yl)-2-(Z)-methoxyiminoacetamido]-3-[(5RS)-2-oxotetrahydrofuran-5-yl]ceph-3-em-4-carboxylic acid,
(6R,7R)-7-[2-(2-aminothiazol-4-yl)-2-(Z)-hydroxyiminoacetamido]-3-[(5RS)-2-oxotetrahydrofuran-5-yl]ceph-3-em-4-carboxylic acid,
(6R,7R)-7-[2-(2-aminothiazol-4-yl)-2-(Z)-methoxyiminoacetamido]-3-[(4RS-2-oxotetrahydrofuran-4-yl]ceph-3-em-4-carboxylic acid,
(6R,7R)-7-[2-(2-aminothiazol-4-yl)-2-(Z)-carboxymethoxyiminoacetamido]-3-[(5RS)-2-oxotetrahydrofuran-5-yl]ceph-3-em-4-carboxylic acid, and
(6R,7)-7-[2-(2-aminothiazol-4-yl)-2-(Z)-methoxyiminoacetamido]-3-[(3RS)-2-oxotetrahydrofuran-3-yl]ceph-3-em-4-carboxylic acid.

12. Pivaloyloxymethyl (6R,7R)-7-[2-(2-aminothiazol-4-yl)-2-(Z)-methoxyiminoacetamido]-3-[(5RS)-2-oxotetrahydrofuran-5-yl]ceph-3-em-4-carboxylate.

13. A pharmaceutical composition comprising a compound of formula (Ia) or a pharmaceutically acceptable salt or in vivo hydrolysable ester thereof, as defined in claim 10, and a pharmaceutically acceptable carrier.

14. A pharmaceutical composition according to claim 13 further comprising a β-lactamase inhibitor.

15. A method of treating bacterial infections in humans and animals which comprises the administration of a therapeutically effective amount of a compound of formula (Ia) or a pharmaceutically acceptable salt or in vivo hydrolysable ester thereof, as defined in claim 10.

* * * * *